United States Patent [19]

Lackey et al.

[11] Patent Number: 5,342,947
[45] Date of Patent: Aug. 30, 1994

[54] PREPARATION OF WATER SOLUBLE CAMPTOTHECIN DERIVATIVES

[75] Inventors: Karen Lackey, Durham; Daniel D. Sternbach, Chapel Hill, both of N.C.

[73] Assignee: Glaxo Inc., Research Triangle Park, N.C.

[21] Appl. No.: 960,498

[22] Filed: Oct. 9, 1992

[51] Int. Cl.5 .................................. C07D 491/147
[52] U.S. Cl. ............................. 546/41; 546/48; 544/60; 544/125; 544/361; 540/470; 540/481; 540/575; 540/597
[58] Field of Search .............. 546/41, 48; 514/279, 514/283; 562/586; 564/209

[56] References Cited

U.S. PATENT DOCUMENTS

| | | | |
|---|---|---|---|
| 2,922,816 | 1/1960 | Bruce | 564/209 |
| 3,972,925 | 8/1976 | Souter | 564/209 |
| 3,985,723 | 10/1976 | Panetta | 564/209 |
| 4,399,276 | 8/1983 | Miyasakawa | 564/48 |
| 4,473,692 | 9/1984 | Miyasakawa | 546/48 |
| 4,545,880 | 10/1985 | Miyasakawa | 204/158 |
| 4,778,891 | 10/1988 | Tagawa et al. | 546/92 |
| 4,894,456 | 1/1990 | Wall | 546/41 |
| 4,943,579 | 7/1990 | Vishnuvajjala | 514/283 |
| 4,981,968 | 1/1991 | Wall et al. | 546/41 |
| 5,049,668 | 9/1991 | Wall et al. | 546/48 |
| 5,053,512 | 10/1991 | Wani et al. | 546/41 |

FOREIGN PATENT DOCUMENTS 321122  6/1989  European Pat. Off. ............. 546/48

OTHER PUBLICATIONS

Kingsbury, et al., J. Med. Chem., 34, 98 (1991).
Lui, F., CRC Critical Review in Biochem., 1-24, 15 (1983).
Vosberg, H., Current Topics in Microbio. and Immu., 19, Springer-Verlag, Berlin, (1985).
Giovanella, et al., Science, 246, 1046 (1989).
Wani et al., J. Med. Chem., 30, 2317-2319 (1987).
Wani et al., J. Med. Chem., 29, 235-63 (1986).
March, Advanced Organic Chem., 3rd Ed, p. 179, John Wiley & Sons, NY (1925).
Lehninger, A., Principles of Biochem., 813, Worth Publishers, NY (1982).
Wani et al., J. Med. Chem., 23, 554-560 (1980).
Sugasawa, et al., J. Org. Chem., 44, No. 4, 578 (1979).
Wall and Wani, Ann. Rev. Pharmacol, Toxical, 17, 117 (1977).
Abbott, Cancer Treatment Reports, 60, No. 8, 1007 (1976).
Schultz, Chem. Rev., 73, No. 4, 385 (1973).
Wani et al., J. Am. Chem. Soc., 99, 3631 (1972).
Muggia, et al., Canc. Chemo. Reports, 56, No. 56, No. 4, 515 (1972).
Gottlieb et al., Canc. Chemo. Reports, 54, No. 6, (1970).
Jaxel, et al., Cancer Research, 49, 1465 (1989).
Giovanella, et al., Cancer, 52, 1146 (1983).
Boven, et la., The Nude Mouse in Oncology Research, CRC Press, Boca Raton, Fla. (1991).
Fiebig, Human Tumor Xenographs in Anticancer Drug Dev., "Comparison of Tumor Response in Nude Mice and in Patients," Winograd, et al., Eds. ESO Monographs, Springer, Heidelberg, 25 (1988).

Primary Examiner—Donald G. Daus
Attorney, Agent, or Firm—Charles T. Joyner

[57] ABSTRACT

The present invention relates to the synthesis of water soluble, camptothecin derivatives of formula (I),

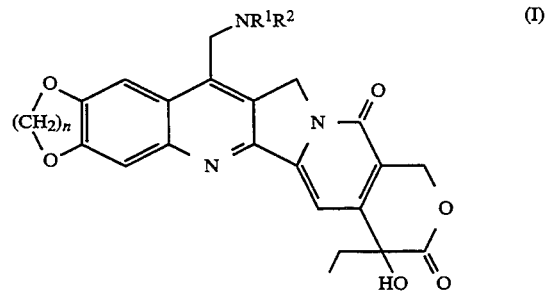

wherein:

n represents the integer 1 or 2;

$R^1$ represents independently, hydrogen, lower alkyl, ($C_{3-7}$)cycloalkyl, ($C_{3-7}$)cycloalkyl lower alkyl, lower alkenyl, hydroxy lower alkyl, lower alkoxy lower alkyl; and $R^2$ represents hydrogen and the pharmaceutically acceptable salts thereof.

5 Claims, No Drawings

PREPARATION OF WATER SOLUBLE CAMPTOTHECIN DERIVATIVES

The present invention relates to water soluble, camptothecin derivatives substituted in the 7 position, their use in the treatment of tumors and methods of their preparation.

BACKGROUND OF THE INVENTION

Camptothecin, a natural, cytotoxic alkaloid, is a topoisomerase I inhibitor and potent antitumor agent. It was first isolated from the leaves and bark of the Chinese plant, *Camptotheca accuminata*, by Wall, et al. (*J. Am. Chem. Soc.*, 88 3888 (1966)).

As depicted, camptothecin is a fused ring system, composed of a quinoline (A and B), fused to a pyrrolidine ring (C), fused to an alpha-pyridone ring (D) which in turn is fused to a lactone ring (E).

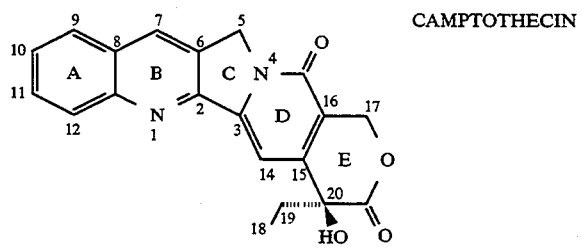

CAMPTOTHECIN

It has an asymmetric carbon at the 20 position making two enantiomeric forms possible. However, the natural occurring compound is found in the "S" configuration as shown above.

Cytotoxic agents are often employed to control or eradicate tumors i.e., they are chemotherapeutic agents. Camptothecin's cytotoxic activity is thought to be directly related to camptothecin's potency as a topoisomerase inhibitor. [For detailed explanations of the topoisomerase function see A. Lehninger, *Principles of Biochemistry*, 813, Worth Publishers, New York (1982); L. F. Liu, "DNA Topoisomerases," *CRC Critical Review in Biochemistry*, 1-24, 15 (1983) and H Vosberg, "DNA Topoisomerases: Enzymes that Control DNA Conformation," *Current Topics in Microbiology and Immunology*, 19, Springer-Verlag, Berlin (1985).] In particular, camptothecin has been shown to be effective in the treatment of leukemia (L-1210) and certain solid tumors in laboratory animals, e.g., see *Chem. Rev. 23*, 385 (1973) and *Cancer Treat. Rep., 60*, 1007 (1967).

Unfortunately, in the clinic camptothecin's promise as an effective antitumor agent has not been completely fulfilled. Camptothecin is essentially insoluble in physiologically compatible, aqueous media, and must be modified to make it sufficiently soluble for parenteral administration, a preferred mode for antitumor treatment. It can be made soluble by forming its sodium salt, that is, by opening the lactone with sodium hydroxide (see F. M. Muggia, et al., *Cancer Chemotherapy Reports*, pt. 1, 56, No.4, 515 (1972)). However, M. C. Wani, et al., *J. Med. Chem, 23*, 554 (1980), reported that the alpha-hydroxy lactone moiety of ring E is an absolute requirement for antitumor activity.

In the art there are examples of modifications and derivatives of camptothecin prepared to improve its solubility in water. Although many of these derivatives were active in in vitro and in early animal studies using leukemia (L-1210) models, they were disappointing in chronic, animal models involving implanted solid tumors.

Miyasaka, et al., U.S. Pat. No. 4,399,282, discloses a group of camptothecin derivatives substituted at the 7 position with, inter alia, hydroxymethyl and alkoxymethyl. Further, Miyasaka, et. al. in U.S. Pat. No. 4,399,276 discloses camptothecin-7-aldehyde and certain related aldehyde derivatives such as acetals, oximes and hyrazones. More recently, Vishnuvajjala, et al., in U.S. Pat. No. 4,943,579, claimed a series of water-soluble camptothecin derivatives with substituents on the A ring as does Boehm, et al., European Patent application 0 321 122 A2. Other examples of derivatives of camptothecin include Miyasaka, et al., U.S. Pat. No. 4,473,692 and U.S. Pat. No. 4,545,880; and W. Kingsbury, et al., *J Med. Chem.*, 34, 98 (1991). None of these references reported compounds with antitumor activity greater than that of camptothecin itself.

Wani and co-workers reported that 10, 11-methylenedioxycamptothecin is more potent than unsubstituted camptothecin (see M. C. Wani, et al., *J. Med. Chem*, 29, 2358 (1986) and 30, 2317 (1987)). However, its water solubility is as poor as camptothecin which seriously limits its clinical utility.

We have now found water-soluble analogs of camptothecin with good, topoisomerase I inhibitory activity in vitro, and impressive, antitumor activity in vivo.

SUMMARY OF THE INVENTION

One aspect of the present invention are the water-soluble camptothecin analogs of formula (I),

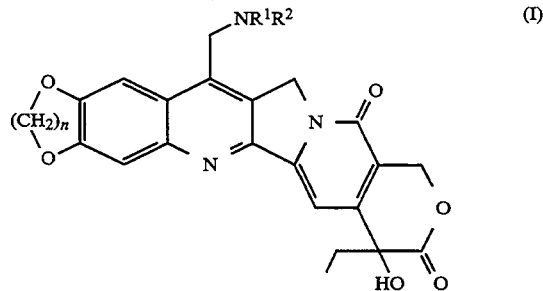

wherein:

n represents the integer 1 or 2; and i) $R^1$ and $R^2$ represent independently, hydrogen, lower alkyl, ($C_{3-7}$)cycloalkyl, ($C_{3-7}$)cycloalkyl lower alkyl, lower alkenyl, hydroxy lower alkyl, lower alkoxy lower alkyl; or ii) $R^1$ represents hydrogen, lower alkyl, ($C_{3-7}$)cycloalkyl, ($C_{3-7}$)cycloalkyl lower alkyl, lower alkenyl, hydroxy lower alkyl or lower alkoxy lower alkyl, and $R^2$ represents —$COR^3$, wherein: $R^3$ represents hydrogen, lower alkyl, perhalo-lower alkyl, ($C_{3-7}$)cycloalkyl, ($C_{3-7}$)cycloalkyl lower alkyl, lower alkenyl, hydroxy lower alkyl, lower alkoxy, lower alkoxy lower alkyl; or iii) $R^1$ and $R^2$ taken together with the linking nitrogen form a saturated 3 to 7 atom heterocyclic group of formula (IA)

wherein: Y represents O, S, SO, SO$_2$, CH$_2$ or NR$^4$ wherein: R$^4$ represents hydrogen, lower alkyl, perhalo lower alkyl, aryl, aryl substituted with one or more lower alkyl, lower alkoxy, halogen, nitro, amino, lower alkyl amino, perhalo-lower alkyl, hydroxy lower alkyl, lower alkoxy lower alkyl groups or; —COR$^5$, wherein: R$^5$ represents hydrogen, lower alkyl, perhalo-lower alkyl, lower alkoxy, aryl, aryl substituted with one or more lower alkyl, perhalo-lower alkyl, hydroxy lower alkyl, lower alkoxy lower alkyl groups or;
the pharmaceutically acceptable salts thereof.

Pharmaceutically acceptable salts include, but are not limited to salts with inorganic acids such hydrochloride, sulfate, phosphate, diphosphate, hydrobromide and nitrate or salts with an organic acid such as acetate, malate, maleate, fumarate, tartrate, succinate, citrate, lactate, methanesulfonate, p-toluenesulfonate, palmoate, salicylate and stearate. Other acids such as oxalic, while not in themselves pharmaceutically acceptable, may be useful as intermediates in obtaining the compounds of the invention and their pharmaceutically acceptable salts.

The lactone ring, ring E, may be opened by alkali metal or alkaline-earth metal bases, for example sodium hydroxide or calcium hydroxide, to form alkali metal or alkaline-earth metal salts of the corresponding open E ring form of the compounds of formula (I). Because of its better solubility in water, the open E ring form may advantageously be purified by conventional recrystallization techniques. Accordingly, said open E ring form may then be used as an intermediate to form the compounds of formula (I), for example by treatment with acid, e.g., hydrochloric acid, and thereby produce a purified form of the compounds of formula (I).

As noted above, the camptothecin moiety has an asymmetric carbon atom at the 20 position making two enantiomeric forms, i.e., "R" and "S" configurations, possible. This invention includes both enantiomeric forms and any combinations of these forms. For simplicity, where no specific configuration at the 20 position is depicted in the structural formulas, it is to be understood that both enantiomeric forms and mixtures thereof are represented. Unless noted otherwise, the nomenclature convention, "(R,S)", denotes a racemic (approximately equal portion) mixture of the R and S enantiomers while "(R)" and "(S)" denote essential optically pure R and S enantiomers respectively. Also included in the invention are other forms of the compound of formula (I), such as solvates, hydrates, polymorphs and the like.

Another aspect of the invention is a method of inhibiting topoisomerase Type I in mammalian cells comprising administering to a patient a topoisomerase inhibiting amount of a compound of formula (I), and a method of treating a tumor in a mammal comprising administering to a mammal bearing a tumor, an effective antitumor amount of a compound of formula (I). A further aspect comprises pharmaceutical formulations containing a compound of formula (I) as an active ingredient. Methods of preparation of the compounds of formula (I) and the associated novel chemical intermediates used in the synthesis, as taught herein, are also within the scope of the present invention.

DETAILED DESCRIPTION OF THE INVENTION

Compounds

As used herein the term "lower" in reference to alkyl and alkoxy means 1–6 carbons and in reference to alkenyl means 3–6 carbons (provided that the double bond is not attached to the carbon which is attached to the nitrogen). The term "perhalo" means all hydrogens have been replaced with a halogen, for example, perhalo lower-alkyl, e.g., trifluoromethyl. The term "aryl" means phenyl or napthyl.

One group of compounds according to the invention are the compounds of formula (I) wherein:
n represents the integer 1 or 2; and
i) R$^1$ and R$^2$ represent independently, hydrogen, lower alkyl (e.g. methyl, ethyl) or hydroxy lower alkyl (e.g. hydroxyethyl);
ii) R$^1$ represents hydrogen and R$^2$ represents —COR$^3$, wherein R$^3$ represents perhalo-lower alkyl (e.g. trifluoromethyl); or
iii) R$^1$ and R$^2$ taken together with the linking nitrogen form azetidine, pyrrolidine, piperidine, morpholine, thiomorpholine or piperazine (optionally N-substituted with lower alkyl (e.g. methyl), phenyl, phenyl substituted with one or more perhalo-lower alkyl (e.g. trifluoromethyl) or lower alkoxy (e.g. methoxy)) or —COR$^5$, wherein R$^5$ represents lower alkyl (e.g. butoxy); and
the pharmaceutically acceptable salts thereof.

A sub group of compounds of formula (I) are those compounds wherein:
R$^1$ and R$^2$ represent: independently, hydrogen, lower alkyl, (C$_{3-7}$) cycloalkyl, (C$_{3-7}$)cycloalkyl lower alkyl, lower alkenyl, hydroxy lower alkyl, lower alkoxy lower alkyl, and Y represents O, S, CH$_2$, NH or N(lower alkyl).

Particular compounds of the above sub group are those wherein:
R$^1$ and R$^2$ represent: independently; hydrogen, (C$_{1-4}$)alkyl, (C$_{3-7}$)cycloalkyl, (C$_{3-7}$)cycloalkyl (C$_{1-4}$)alkyl, (C$_{3-4}$)alkenyl, hydroxy (C$_{1-4}$)alkyl, (C$_{1-4}$)alkoxy (C$_{1-4}$)alkyl, or taken together with the nitrogen form aziridine, azetidine, pyrrolidine, piperidine, hexamethylenimine, imidazolidine, pyrazolidine, isoxazolidine, piperazine, N-methylpiperazine, homopiperazine, N-methylhomopiperazine, thiazolidine, isothiazolidine, morpholine or thiomorpholine.

Specific compounds of formula (I) are:

| Example Number | Compound Name |
| --- | --- |
| 1. | 7-Dimethylaminomethylene-10, 11-methylenedioxy-20(R,S)-camptothecin, |
| 2. | 7-Dimethylaminomethylene-10, 11-methylenedioxy-20(S)-camptothecin, |
| 3. | 7-Dimethylaminomethylene-10, 11-ethylenedioxy-20(R,S)-camptothecin, |
| 4. | 7-Dimethylaminomethylene-10, 11-ethylenedioxy-20(S)-camptothecin, |
| 5. | 7-Morpholinomethylene-10, 11-ethylenedioxy-20(R,S)-camptothecin, |
| 6. | 7-Morpholinomethylene-10, 11-ethylenedioxy-20(S)-camptothecin, |
| 7. | 7-Pyrrolidinomethylene-10, 11-ethylenedioxy-20(R,S)-camptothecin, |
| 8. | 7-Piperidinomethylene-10, 11-methylenedioxy-20(R,S)-camptothecin, |
| 9. | 7-Piperidinomethylene-10, 11-ethylenedioxy-20(R,S)-camptothecin, |
| 10. | 7-(4-Methylpiperazinomethylene)-10, 11-ethylenedioxy-20(R,S)- |

| Example Number | Compound Name |
|---|---|
|  | camptothecin, |
| 11. | 7-(4-Methylpiperazinomethylene)-10, 11-ethylenedioxy-20(S)-camptothecin, |
| 12. | 7-Diethylaminomethylene-10, 11-methylenedioxy-20(S)-camptothecin, |
| 13. | 7-Diethylaminomethylene-10, 11-ethylenedioxy-20(R,S)-camptothecin, |
| 14. | 7-Diethylaminomethylene-10, 11-ethylenedioxy-20(S)-camptothecin, |
| 15. | 7-N-Methylethanolaminomethylene-10, 11-methylenedioxy-20(R,S)-camptothecin, |
| 16. | 7-N-Methylethanolaminomethylene-10, 11-ethylenedioxy-20(RS)-camptothecin, |
| 17. | 7-Diethanolaminomethylene-10, 11-ethylenedioxy-20(R,S)-camptothecin, |
| 18. | 7-Diethanolaminomethylene-10, 11-ethylenedioxy-20(S)-camptothecin, |
| 19. | 7-Azetidinomethylene-10, 11-methylenedioxy-20(R,S)-camptothecin, |
| 20. | 7-Azetidinomethylene-10, 11-methylenedioxy-20(S)-camptothecin, |
| 21. | 7-Thiomorpholinomethylene-10, 11-ethylenedioxy-20(S)-camptothecin, |
| 22. | 7-Azetidinomethylene-10, 11-ethylenedioxy-20(S)-camptothecin, |
| 23. | 7-(4-Methylpiperazinomethylene)-10, 11-methylenedioxy-20(S)-camptothecin, |
| 24. | 7-Trifluoroacetamidomethylene-10, 11-ethylenedioxy-20(S)-camptothecin |
| 25. | 7-Trifluoroacetamidomethylene-10, 11-methylenedioxy-20(S)-camptothecin |
| 26. | 7-Aminomethylene-10, 11-ethylenedioxy-20(S)-camptothecin dihydrochloride, |
| 27. | 7-Aminomethylene-10, 11-methylenedioxy-20(S)-camptothecin dihydrochloride, |
| 28. | 7-tert-Butyloxycarbonyl-piperazinomethylene-10, 11-ethylenedioxy-20(S)-camptothecin, |
| 29. | 7-Piperazinomethylene-10, 11-ethylenedioxy-(S)-camptothecin trifluoroacetic acid salt, |
| 30. | 7-($\alpha,\alpha,\alpha$-Trifluoro-m-tolyl)-piperazinomethylene-10, 11-ethylenedioxy-20(S)-camptothecin, |
| 31. | 7-(2-Methoxyphenyl-piperazino)methylene-10, 11-ethylenedioxy-20(S)-camptothecin and |
| 32. | 7-Phenylpiperazinomethylene-10, 11-ethylenedioxy-20(S)-camptothecin |

Preparation of Compounds

The compounds of the present invention may be prepared by the procedure shown in Scheme I:

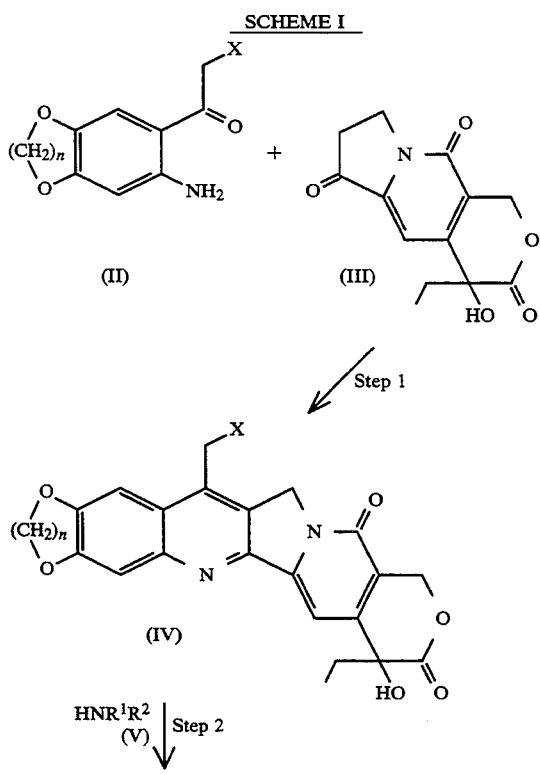

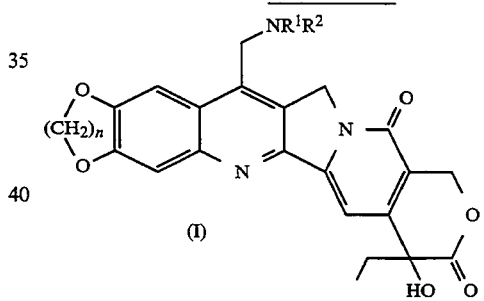

In Step 1 of Scheme I, a compound of formula (II), wherein X is a leaving group (as defined in J. March, *Advanced Organic Chemistry*, 3rd. Ed., page 179, John Wiley & Sons, New York (1985)), for example, a halogen, e.g., chloro, may be reacted with a compound of formula (III) according to the method taught in U.S. Pat. No. 4,894,456 (hereinafter, '456), issued Jan. 16, 1990 to Wall et al., incorporated herein by reference, to yield a compound of formula (IV).

In Step 2, i.e., general process (A), the compounds of formula (IV) may be converted to the compounds of formula (I) by displacement of the leaving group, X, with a compound of formula (V), wherein $R^1$ and $R^2$ are as defined for formula (I). This displacement reaction may conveniently be carried out in a solvent system, for example water, a ($C_{1-4}$) alkanol, a ($C_{2-4}$) alkylene diol, 1-hydroxy-2-methoxyethane, dimethylacetamide (DMAC), N-methylpyrolidinone, dimethyl formamide (DMF), tetrahydrofuran (THF), dimethyl sulfoxide (DMSO), toluene or a combination of these solvents in the presence of excess amine, i.e., excess compound of formula (V), with or without a base, e.g., potassium carbonate.

This method is particularly useful for preparing compounds of formula (I) wherein neither R¹ nor R² are hydrogen.

An alternate method for preparing the compounds of the present invention is shown in Scheme 1A:

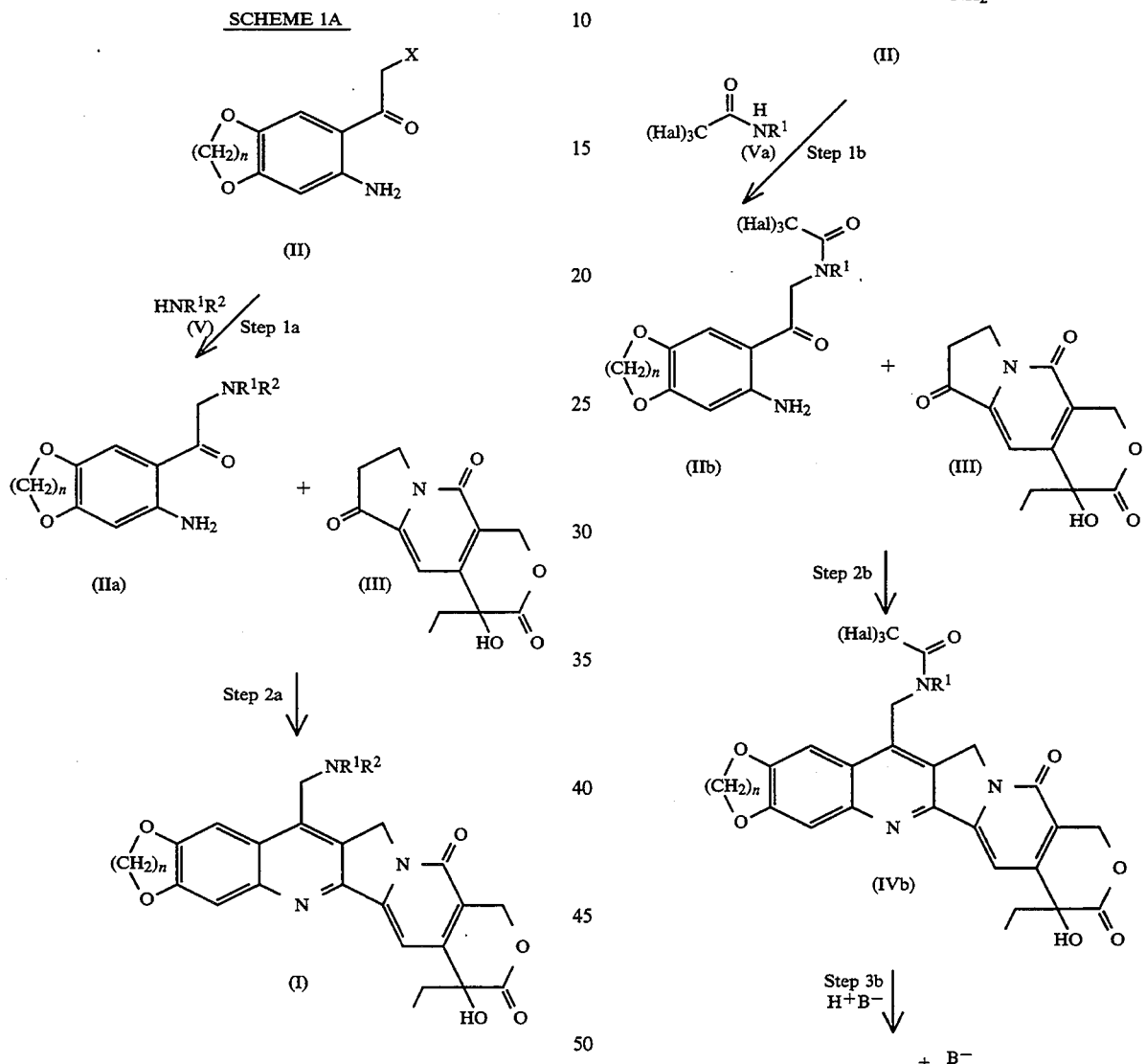

In Step 1a, a compound of formula (V) is reacted with a compound of formula (II) to yield a compound of formula (IIA), wherein R¹ and R² are as defined for the compounds of formula (I). This reaction may be carried out under conditions similar to those described in Scheme 1, Step 2.

In Step 2a, general process (B), compound of formula (IIA) is reacted with a compound of formula (III) in a similar manner to that taught above in Scheme 1, Step 1, to yield a compound of formula (I).

Another alternate method for preparing the compounds of the present invention is shown in Scheme 1B In Step 1b, a compound of formula (Va) (wherein "Hal" is halogen, i.e., fluoro, chloro, bromo or iodo) e.g., trifluoroacetamide, is reacted with a compound of formula (II) in a polar, aprotic solvent, e.g., acetonitrile, in the presence of a base soluble in the polar, aprotic solvent, e.g., cesium carbonate if the solvent is acetonitrile, to yield a compound of formula (IIb).

In Step 2b, a compound of formula (IIb) is reacted with a compound of formula (III) in a similar manner to that taught in Scheme 1, Step 1, yield a compound of formula (IVb).

In Step 3b, general process (C), a compound of formula (IVb) is treated with an acid, H+B−, such as a mineral acid, e.g., hydrochloric acid or sulfuric acid, to yield a compound of formula (Ib), i.e. salt of a compound of formula (I). The compound of formula (Ib) may be treated with a base, such as an alkali metal hydroxide or carbonate, e.g., sodium hydroxide or potassium carbonate, by standard method of the art to yield the corresponding free base. For example a compound of formula (Ib) may be stirred with an aqueous solution of potassium carbonate for about one to about four hours in the temperature range of from about 5° to about 100° C. The free base can then be converted by conventional means to a pharmaceutically acceptable salt if required.

This alternate method is particularly useful for preparing compounds of Formula (I) wherein both $R^1$ and $R^2$ are hydrogen or $R^2$ is hydrogen.

The compounds of formula (II) may be prepared according to the procedure shown in Scheme II:

art, such as those taught in T. Green, *Protective Groups in Organic Chemistry*, Chap. 7, John Wiley, New York (1981). For example, a compound of formula (IX) may be heated at reflux in concentrated hydrochloric acid, and the resulting salt neutralized with a base, e.g., sodium hydroxide, to yield a compound of formula (II).

In Step 2a of Scheme II, when the compound of formula (VI) is the ethylenedioxy compound, i.e., n is equal to 2, it may be reacted directly with a compound of formula (VIII), without first protecting the amino group by acylation, to yield the corresponding compound of formula (II).

Alternatively compounds of formula (II) may be prepared according to the method taught by T. Sugasawa, et al., *J. Org. Chem.*, 44, 578 (1979).

The compound of formula (III) may be prepared according to the procedure of Wall, et al., '456, at column 11, starting at line 30. It is apparent from Scheme 1 that the configuration of the asymmetric carbon of the compound of formula (III) will govern the configuration of the compounds of formula (I). The racemic compound of formula (III) can be resolved into either of its enantiomers by the method of Wani, et al., in U.S. Pat. No. 5,053,512, (hereinafter, "512") incorporated herein by reference.

The novel, intermediate compounds of formulas (II),

SCHEME II

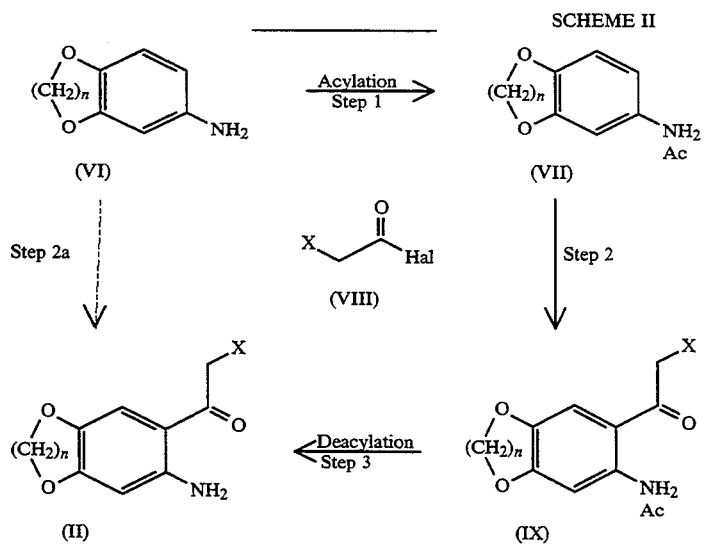

In Step 1 of Scheme II, a compound of formula (VI) is reacted with an acylating agent, for example, a ($C_{2-5}$)alkanoic acid halide or ($C_{2-5}$) alkanoic acid anhydride, e.g., acetyl chloride or acetic anhydride, in the presence of a weak base, for example, potassium carbonate, in a polar, aprotic, solvent, for example, chloroform, to yield a compound of formula (VII), wherein Ac is a ($C_{2-5}$) acyl group.

In Step 2, a compound of formula (VII) is reacted with a compound of formula (VIII), wherein X is a leaving group as defined for the compounds of formula (IV) and Hal is halogen, in the presence of a metalic halide, e.g., zinc chloride, in a polar, aprotic solvent, e.g., nitromethane, to yield a compound of formula (IX). A compound of formula (VIII), for example, may be a haloacetyl halide, e.g., chloroacetyl chloride, or a haloacetonitrile, e.g., chloroacetonitrile.

In Step 3, a compound of formula (II) is formed by removal of the acyl group, Ac, from a compound of formula (IX), i.e., deacylation, by methods known in the (IIA) and (IV) are within the scope of this invention.

According to another general process (D), a compound of formula (I) according to the invention may be converted into another compound of the invention using conventional procedures.

Thus, for example, a compound of formula (I) wherein one or more of $R^1$ and $R^2$ represent a hydrogen atom, may be alkylated using conventional techniques. The reaction may be effected using a suitable aklylating agent such as an alkyl halide, an alkyl tosylate or a dialkylsulphate. the alkylation reaction may conveniently be carried out in an organic solvent such as an amide, e.g. dimethylformamide, or an ether, e.g. tetrahydrofuran, preferably in the presence of a base. Suitable bases include, for example, alkali metal hydrides, such as sodium hydride, alkali metal carbonates, such as sodium carbonate, or potassium methoxide, ethoxide or t-butoxide. The alkylation reaction is conveniently carried out at a temperature of from about 25° to about 100° C.

Alternately, a compound of formula (I) wherein one or more of $R^1$ and $R^2$ represents a hydrogen atom may be converted to another compound of formula (I) by reductive alkylation. Reductive alkylation with an appropriate aldehyde or ketone may be effected using an alkaline earth metal borohydride or cyanoborohydride. The reaction medium, conveniently in an alcohol, e.g. methanol or ethanol or an ether, e.g. dioxan or tetrahydrofuran, optionally in the presence of water. The reaction may conveniently be carried out at a temperature in the range of 0° to 100° C., preferably about 5° to about 50° C.

Alternatively, a compound of formula (I) wherein one or more of $R^1$ and $R^2$ represents a lower alkenyl group may be converted to another compound of formula (I) wherein $R^1$ and $R^2$ represents a lower alkyl group. Reduction may conveniently be effected in the presence of hydrogen and a metal catalyst, for example, Raney nickel or a nobel metal catalyst such as palladium, platinum, platinum oxide or rhodium, which may be supported, for example, on charcoal. The reaction may be effected in a solvent such as an alcohol, for example ethanol and conveniently at a temperature of from about $-10°$ to about $+50°$ C., preferably about 20° to about 30° C.

According to another general process (E), a compound of formula (I) according to the invention, or a salt thereof may br prepared by subjecting a protected derivative of formula (I) or a salt thereof to reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (l) may be used in conventional manner. See for example, "Protective Groups in Organic Chemistry" Ed. J.F.W. McOmie (Plenum Press 1973) or "Protective Groups in Organic Synthesis" by Theodora w. Greene (John Wiley and Sons 1981).

Conventional amino protecting groups may include, for example, aralkyl groups, such as benzyl, diphenylmethyl or triphenylmethyl groups; and acyl groups such as N-benzyloxycarbonyl or t-butoxycarbonyl. Thus, compounds of general formula (l) wherein one or more of the groups $R^1$ and $R^2$ represent hydrogen may be prepared by deprotection of a corresponding protected compound.

Hydroxy groups may be protected, for example, by aralkyl groups, such as benzyl, diphenylmethyl or triphenylmethyl groups, acyl groups, such as acetyl, silicon protecting groups, such as trimethylsilyl or t-butyl dimethylsilyl groups or as tetrahydropyran derivatives.

Removal of any protecting groups present may be achieved by conventional procedures. Thus, an aralkyl groups such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation; silicon protecting groups may be removed, for example, by treatment with fluoride ion or by hydrolysis under acidic conditions; tetrahydropyran groups may be cleaved by hydrolysis under acidic conditions.

As will be appreciated, in any of the general processes (A) to (D) described above, it may be necessary or desired to protect any sensitive groups in the molecule as just described. Thus, a reaction step involving deprotection of a protected derivative of general formula (l) or a salt thereof may be carried out subsequent to any of the above described processes (A) to (D).

Thus, according to a further aspect of the invention, the following reactions may, if necessary and/or desired by carried out in any appropriate sequence subsequent to any of the processes (A) to (D)

(i) removal of any protecting groups; and
(ii) conversion of a compound of formula (l) or a salt thereof into a pharmaceutically acceptable salt thereof.

Where it is desired to isolate a compound of the invention as a salt, for example, as an acid addition salt, this may be achieved by treating the free base of general formula (l) with any appropriate acid, preferably with an equivalent amount, or with creatinine sulphate in a suitable solvent (e.g. aqueous ethanol).

As well as being employed as the last main step in the preparative sequence, the general methods indicated above for the preparation of the compounds of the invention may also be used of the introduction of the desired groups at an intermediate stage in the preparation of the required compound. It should therefore be appreciated that in such multi-stage processes, the sequence of reactions should be chosen in order that the reacting conditions do not affect groups present in the molecule which are desired in the final product.

The biological activity of the compounds of formula (l) appears to reside in the S enantiomer, and the R enantiomer has little or no activity. Thus, the S enantiomer of a compound of formula (l) is generally preferred over a mixture of R and S such as the racemic mixture. However, if the R enantiomer were desired, e.g., for control studies or synthesis of other compounds, it could be conveniently prepared by the procedure above using the R enantiomer of the compound of formula (lll) prepared according to the teachings of '512.

A compound of formula (I) prepared by reaction Scheme I or Scheme I, be purified by conventional methods of the art, e.g., chromatography, distillation or crystallization.

Cleavable Complex in vitro Assay

The data in Table A, below, shows the relative topoisomerase Type I inhibitory activity of the compounds of Formula (I). This assay performed according to the method described in Hsiang, Y. et al., *J. Biol. Chem.*, 260:14873–14878 (1985), correlates well with in vivo anti-tumor activity of topoisomerase inhibitors in animal models of cancer, e.g., camptothecin and its analogs. See Hsiang et al., *Cancer Research*, 49:4385–4389 (1989) and Jaxel et al., *Cancer Research*, 49:1465–1469 (1989).

Those compounds which exhibit observable activity at concentrations greater than 2000 nM ("+" in Table A) are considered weakly to moderately active, while those with activity at concentrations less than 500 nM ("++++" in Table A) are very active. The term "$IC_{50}$" means the concentration of a compound of formula (I) at which 50% of the DNA substrate has been captured by topoisomerase I.

TABLE A

Topoisomerase Inhibitory Activity of

TABLE A-continued

Compounds of Formula (I) in the Cleavable Complex Assay

| Example Number | Isomeric form | Relative IC$_{50}$* |
|---|---|---|
| 2 | (S) | ++++ |
| 6 | (S) | ++++ |
| 11 | (S) | ++++ |
| 1 | (R,S) | ++++ |
| 17 | (R,S) | ++++ |
| 5 | (R,S) | ++++ |
| 4 | (S) | +++ |
| 9 | (R,S) | +++ |
| 10 | (R,S) | +++ |
| 13 | (R,S) | +++ |
| 16 | (R,S) | ++ |
| 7 | (R,S) | ++ |
| 15 | (R,S) | ++ |
| 16 | (R,S) | ++ |
| 19 | (R,S) | ++ |
| 8 | (R,S) | + |

*IC$_{50}$ Range

| Symbol | nM |
|---|---|
| ++++ | <~500 |
| +++ | <~1000 > ~500 |
| ++ | <~2000 > ~1000 |
| + | >~2000 |

The compounds of formula (IV) have also been found to have good topoisomerase I inhibitory activity.

Human Tumor Xenografts

In recent years, human tumor xenografts heterotransplanted into nude mice have been widely used to assess the antitumor activities of cancer chemotherapeutic agents. See Giovanella, B. C., Stehlin, Jr., J. S., Shepard, R. C. and Williams, Jr., L. J., "Correlation between response to chemotherapy of human tumors in patients and in nude mice", Cancer 52:1146–1152, (1983); Boven, E. and Winograd, B, Eds. *The Nude Mouse in Oncology Research* CRC Press, Inc., Boca Raton, FL, (1991); and Fiebig, H. H., "Comparison of tumor response in nude mice and in patients", *Human Tumour Xenografts in Anticancer Drug Development*, Winograd, B., Peckham, M. J., and Pinedo, H. M., Eds., E.S.O. Mongraphs, Springer, Heidelberg, 25 (1988).

In general, human tumor xenografts retain not only the histological, biochemical and antigenic characteristics, but also the chemosensitivity of the tumor tissue of origin (Boven, et al., supra). Lengthy studies have provided evidence that human tumor xenografts retain these important biological properties of the tumor of origin including a biological instability as is known to occur in patient's tumors (Boven, et al., supra). Most importantly, several investigators have reported good correlations between drug effects in the human tumor xenografts and clinical results in human patients (Giovanella, et al., and Fiebig supra).

Human Colorectal Adenocarcinoma HT-29 Xenograft in vivo Assay

Female NU/NU mice weighing 21±2 g, are used for this modified version of the test described by B. C. Giovanella, et al., *Science*, 246 1046 (1989). Control and test animals are injected subcutaneously in the subscapular region with a suspension of $10^6$ viable HT-29 human colon tumor cells on day 0. Tumors are allowed to grow for 2 weeks prior to drug administration. For each drug, several doses are chosen based on its in vitro activity against topoisomerase I. Each dose level group contains 8 animals. The test compounds are prepared in either 0.1M acetate buffer, pH 5 (vehicle "a") or 87.5% phosphate buffered saline, 12.375% dimethylsulfoxide, and 0.125% Tween 80 (trademark of ICI America for polyoxyethylenesorbitan monooleate) (vehicle "b") and are administered subcutaneously twice a week for 5 weeks beginning on day 14. Doses are given on a mg/kg basis according to the mean body weight for each cage.

Tumor weight is calculated from two perpendicular caliper measurements of the tumor using the formula, tumor weight=length×width$^2$÷2 in millimeters. For each animal, tumor weight is monitored over the course of the experiment. For each group, the results are expressed as the ratio of the mean tumor weight immediately after 5 weeks of treatment (day 50) divided by the mean tumor weight immediately before treatment (day 14). Results are expressed in Table B. For either of the vehicle controls, the ratio is approximately 20, indicating that the tumor, in the absence of drug treatment, increased in weight approximately 20-fold over the course of the experiment. In contrast, a ratio of 1 indicates tumor stasis while a ratio less than 1 indicates tumor regression. Thus, compounds 4 and 6 caused tumor stasis while compounds 11 and 23 caused tumor regression. The criterion for antitumor activity is at least 50% inhibition of tumor growth after 5 weeks of dosing (day 50), giving a ratio of less than or equal to ten.

TABLE B

Optimal Dose in vivo Antitumor activity

| Compound | (mg/kg) | (tumor wt$_{day\ 50}$/tumor wt$_{day\ 14}$) |
|---|---|---|
| control (vehicle alone) | — | 20.0$^a$, 21.8$^b$ |
| 2 | 0.8 | 1.8$^b$ |
| 4 | 7.0 | 1.3$^a$, 1.0$^b$ |
| 6 | 1.0 | 1.0$^b$ |
| 11 | 9.0 | 0.6$^a$ |
| 14 | 2.0 | 2.0$^a$ |
| 20 | 1.5 | 1.5$^a$ |
| 22 | 12.0 | 1.6$^a$ |
| 23 | 3.0 | 0.5$^a$ |

$^a$vehicle of 0.1M acetate buffer, pH 5.
$^b$vehicle of 87.5% phosphate buffered saline, 12.375% dimethylsulfoxide, and 0.125% Tween 80.

Utility

In view of such activity, the compounds of formula (I) are active against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, etc. Herein the terms "tumor", "cancer" and "cancerous growths" are used synonymously.

The amount of compound of formula (I) required to be effective as an antitumor agent will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective antitumor dose is in the range of about 0.1 to about 200 mg/kg body weight per day, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 75 to about 7500 mg per day, and a typical dose would be about 800 mg per day. If discrete multiple doses are indicated, treatment might typically be 200 mg of a compound of formula (I) given 4 times per day.

Formulations

Formulations of the present invention, for medical use, comprise an active compound, i.e., a compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal or vaginal administration may be presented as a suppository with a conventional carrier, e.g., cocoa butter or Witepsol S55 (trademark of Dynamite Nobel Chemical, Germany, for a suppository base).

For transdermal administration, the compounds according to the invention may be formulated as creams, gels, ointments or lotions or as a transdermal patch. Such compositions may, for example, be formulated with an aqueous or oily base with the addition of suitable thickening, gelling, emulsifying, stabilizing, dispersing, suspending and/or coloring agents.

Formulations suitable for parenteral administration conveniently comprise a sterile aqueous preparation of the active compound which is preferably isotonic with the blood of the recipient. Such formulations suitably comprise a solution or suspension of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride. Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the *Journal of the American Chemical Society*. As used here in the term "room temperature" means about 25° C.

EXAMPLE 1

7-Dimethylaminomethylene-10, 11-methylenedioxy-20(R,S)-camptothecin (Compound 1)

(A) 3,4-Methylenedioxyacetanilide

To commercially available 3,4-methylenedioxy aniline (17.0 g, 124 mmol) and sodium carbonate (15.5 g, 136 mmol) in chloroform (90 mL) at 5° C. is added acetyl chloride (8.8 g, 124 mmol) dropwise with stirring. The reaction is allowed to warm to room temperature and stirring is continued for about 18 hours. The reaction mixture is washed twice with about 50 mL of 1N HCl and the organic layer is dried (MgSO$_4$) and the solvent removed to yield a brown solid. Recrystallization from water with activated carbon treatment yields 3,4-methylenedioxyacetanilide (9.34 g, 42.1% of theory) as a light brown solid. Elemental analysis: (C$_9$H$_9$NO$_3$):

|  | % C | % H | % N |
|---|---|---|---|
| Found: | 60.34 | 5.04 | 7.79 |
| Calculated | 60.33 | 5.06 | 7.82 |

(B) 2'-Acetylamino-4',5'-methylenedioxy-2-chloroacetophenone

To a mixture of zinc chloride (24.3 g, 178.3 mmol) and chloroacetylchloride (16.1 mL, 202.1 mmol) in nitromethane (85 mL), under nitrogen, at room temperature, with stirring, is added, dropwise, 3,4-methylenedioxyacetanilide (8.96 g, 50.0 mmol) in nitromethane (15 mL). This mixture is then heated at reflux for 1.5 hrs, allowed to cool to room temperature, poured over ice, extracted with methylene chloride, which is then removed by evaporation, to yield a brown solid. This solid is recrystallized from an ethyl acetate/hexane mixture (including treatment with activated charcoal) to yield 2'-acetylamino-4',5'-methylenedioxy-2-chloroacetophenone (831.3 mg, 6.5% of theory) as yellow crystals. $^1$H-NMR (CDCl$_3$): δ 8.45 (s, 1H); 7.2 (s, 1H); 6.09 (s, 2H); 4.65 (s, 2H); 2.25 (s, 3H).

(C) 3,4-Methylenedioxypivaloylanilide

This compound is prepared by the method of Example 1(a) except an equivalent amount of 2,2-dimethylpropanoyl chloride is used in place of acetyl chloride.

(D) 2'-Pivoylamino-4',5'-methylenedioxy-2-chloroacetophenone

This compound is prepared by the method of Example 1(B) except an equivalent amount of 3,4-methylenedioxypivaloylanilide is used in place of 3,4-methylenedioxyacetanilide.

(E) 2'-Amino-4',5'-methylenedioxy-2-chloroacetophenone

To 2'-acetylamino-4',5'-methylenedioxy-2-chloroacetophenone (0.9 g, 3.53 mmol) or an equivalent amount of 2'-pivoylamino-4',5'-methylenedioxy-2-chloroacetophenone in ethanol (60 mL) at about 5° C. is added, dropwise, conc. HCl (12.5 mL, 149.7 mmol). The reaction mixture is then heated at reflux for about an hour, then poured over 2N NaOH/ice (80 mL/60 g) and washed with ethyl acetate (3×70 mL). The organic portions are combined and washed with brine (50 mL), dried (anhydrous sodium sulfate) and concentrated in vacuo to yield a greenish-yellow solid. This solid is recrystallized from ethyl acetate/isopropanol/hexane, treated with activated charcoal, to yield 2'-amino-4',5'-methylenedioxy-2-chloroacetophenone (0.39 g, 52% of theory).

Elemental analysis: (C$_9$H$_8$NO$_3$Cl)

|  | % C | % H | % N |
|---|---|---|---|
| Found: | 50.66 | 3.80 | 6.47 |
| Calculated | 50.60 | 3.77 | 6.56 |

(F) 5'(R,S)-1,5-Dioxo-(5'-ethyl-5'-hydroxy-2'H,5'H,6'H,6-oxopyrano)[3', 4'-f]Δ$^{6,8}$-tetrahydroindolizine and 5'(S)-1,5-Dioxo-(5'-ethyl-5'-hydroxy-2'H,5'H, 6'H-6-oxopyrano)[3', 4'-f]Δ$^{6,8}$-tetrahydroindolizine (compounds of formula (III))

These compounds, referred to hereinafter as "tricyclic ketone (R,S)" and "tricyclic ketone (S)" respectively or collectively as "a compound of formula (III)", are prepared according to the procedure taught by Wani et al., in '512. Note that the corresponding R enantiomer may also be prepared by the procedure of '512.

(G) 7-Chloromethyl-10,11-methylenedioxy-20(R,S)-camptothecin

Following the general procedure for camptothecin taught in '512, 2'-amino-4',5'-methylenedioxy-2-chloroacetophenone is stirred in refluxing toluene (50 mL) with tricyclic ketone (R,S) (256.3 mg, 0.97 mmol) under a Dean-Stark trap for half an hour. The reaction is then cooled and the solid filtered and washed with toluene and ethanol to yield 7-chloromethyl-10,11-methylenedioxy-20(R,S)-camptothecin, (408.5 mg, 68.8%). $^1$H-300 NMR (DMSO-d6): δ 7.72 (s, 1H); 7.55 (s, 1H); 7.2 (s, 1H); 6.34 (s, 2H); 5.42 (s, 2H); 5.32 (s, 2H); 5.24 (s, 2H); 1.85 (m, 2H); 0.88 (t, 3H).

Nominal Mass Spectrum M+1: Calcd.: 441 Found: 441

(H) 7-Dimethylaminomethylene-10, 11-methylenedioxy-20(R,S)-camptothecin

To a stirred mixture of 7-chloromethyl-10, 11-methylenedioxy-(R,S)-camptothecin (0.11 g, 0.25 mmol) and potassium carbonate (346 mg, 0.5 mmol) in dimethylformamide (DMF) (1 mL) is added dimethylamine (6.1 mL, 0.5 mmol) in the form of a 3.73 mg/mL solution in tetrahydrofuran at about 5° C. The reaction mixture is securely stoppered, allowed to warm to room temperature, stirred for about 15 hrs and then filtered to remove the solid material. The filtrate is concentrated by vacuum evaporation and the resulting solid triturated with acetonitrile and filtered. The filtrate is concentrated by vacuum evaporation to a thick residue. The residue is dissolved in minimal amount of chloroform and chromatographed on 30 grams of flash grade silica gel eluting with successive portions of 250 mls of ethyl acetate followed by 250 mls of (9:1 ethyl acetate, isopropanol finally with 250 mls of (4:1 ethyl acetate, isopropanol). Fractions were collected and monitored by TLC (5% methanol, ethyl acetate) and visualized by a UV lamp. The appropriate fractions were pooled, concentrated and dried under vacuo to yield 7-dimethylaminomethylene-10, 11-methylenedioxy-20(R,S)-camptothecin (6.0 mg, 4.7%). This compound was charterized as its acetic acid salt.

m.p. >250° C. Elemental analysis: (C$_{24}$H$_{23}$N$_3$O$_3$C$_2$H$_4$O$_2$):

|  | % C | % H | % N |
|---|---|---|---|
| Found: | 61.64 | 5.17 | 8.73 |
| Calculated | 61.29 | 5.34 | 8.25 |

(I) Open E ring form

The compound of part (H) is treated with an equivalent amount of sodium hydroxide to form the corresponding open E ring form. Treatment of the latter with an equivalent amount of hydrochloric acid closes the E ring and thereby reforms the compound of part (H).

EXAMPLE 2

7-Dimethylaminomethylene-10,
11-methylenedioxy-20(S)-camptothecin (Compound 2)

(A)
7-Chloromethyl-10,11-methylenedioxy-20(S)-camptothecin

This compound is prepared by the procedure of Example 1, except in part (G) an equivalent amount of tricyclic ketone (S) is used in place of tricyclic ketone (R,S).
m.p. >250° C.

(B) 7-Dimethylaminomethylene-10,
11-methylenedioxy-20(S)-camptothecin

This compound is prepared by the procedure of Example 1, part (H), except that an equivalent amount of 7-chloromethyl-10, 11-methylenedioxy-20(S)-camptothecin, prepared according Example 2, part (A), is used in place of 7-chloromethyl-10,11-methylenedioxy-20(R,S)-camptothecin.
m.p. >250° C.
Nominal Mass Spectrum M+1: Calcd.: 450. Found: 450.

EXAMPLE 3

7-Dimethylaminomethylene-10,
11-ethylenedioxy-20(R,S)-camptothecin (Compound 3)

(A)
7-Chloromethyl-10,11-ethylenedioxy-20(R,S)-camptothecin

This compound is prepared by the procedure of Example 1, except in parts (A) and (C) an equivalent amount of 3,4-ethylenedioxy aniline is used in place of 3,4-methylenedioxy aniline.
High Resolution Mass Spectrum M+1: Calcd.: 455.1009. Found: 455.1005

(B) 7-Dimethylaminomethylene-10,
11-ethylenedioxy-20(R,S)-camptothecin

This compound is prepared by the procedure of Example 1, part (H), except that an equivalent amount of 7-chloromethyl-10,11-ethylenedioxy-20(R,S)-camptothecin is used in place of 7-chloromethyl-10,11-methylenedioxy-20(R,S)-camptothecin.
High Resolution Mass Spectrum: Calcd.: 464.1821. Found: 464,1833.

EXAMPLE 4

7-Dimethylaminomethylene-10,
11-ethylenedioxy-20(S)-camptothecin (Compound 4)

(A)
7-Chloromethyl-10,11-ethylenedioxy-20(S)-camptothecin

This compound is prepared by the procedure of Example 1 except in parts (A) and (C) an equivalent amount of 3,4-ethylenedioxy aniline is used in place of 3,4-methylenedioxy aniline, and in part (G) an equivalent amount of tricyclic ketone (S) is used in place of tricyclic ketone (R,S)
High Resolution Mass Spectrum M+1: Calcd.: 455.1009. Found: 455.1000.

(B) 7-Dimethylaminomethylene-10,
11-ethylenedioxy-20(S)-camptothecin

This compound is prepared by the procedure of Example 1, part (H), except that an equivalent amount of 7-chloromethyl-10,11-ethylenedioxy-20(S)-camptothecin in place of 7-chloromethyl-10,11-methylenedioxy-20(R,S)-camptothecin.
High Resolution Mass Spectrum: Calcd.: 464.1821. Found: 464.1811.

EXAMPLE 5

7-Morpholinomethylene-10,11-ethylenedioxy-20(R,S)-camptothecin (Compound 5)

The same procedure as Example 1, part (H), is used except that an equivalent amount of morpholine is used in place of dimethylamine and an equivalent amount of 7-chloromethyl-10,11-ethylenedioxy-20(R,S)-camptothecin, prepared according to Example 3, part (B), is used in place of 7-chloromethyl-10,11-methylenedioxy-20(R,S)-camptothecin.
High Resolution Mass Spectrum: Calcd: 506.1942. Found: 506.1925.

EXAMPLE 6

7-Morpholinomethylene-10,11-ethylenedioxy-20(S)-camptothecin (Compound 6)

The same procedure as Example 1, part (H), is used except that an equivalent amount of morpholine is used in place of dimethylamine and an equivalent amount of 7-chloromethyl-10,11-ethylenedioxy-20(S)-camptothecin, prepared according to Example 4, part (B), is used in place of 7-chloromethyl-10,11-methylenedioxy-20(R,S)-camptothecin.
High Resolution Mass Spectrum: Calcd.: 506.1942. Found: 506.1929.

EXAMPLE 7

7-Pyrrolidinomethylene-10,11-ethylenedioxy-20(R,S)-camptothecin (Compound 7)

The same procedure as Example 1, part (H), is used except that an equivalent amount of pyrrolidine is used in place of dimethylamine and an equivalent amount of 7-chloromethyl-10,11-ethylenedioxy-20(R,S)-camptothecin, prepared according to Example 3, part (A), is used in place of 7-chloromethyl-10,11-methylenedioxy-20(R,S)-camptothecin.
High Resolution Mass Spectrum: Calcd.: 490.1978. Found: 490.1988.

EXAMPLE 8

7-Piperidinomethylene-10,11-methylenedioxy-20(R,S)-camptothecin (Compound 8)

The same procedure as Example 1, part (H), is used except that an equivalent amount of piperidine is used in place of dimethylamine.
$^1$H-300 NMR (DMSO-d6): $\delta$ 7.95 (s, 1H); 7.62 (s, 1H); 7.29 (s, 1H); 6.35 (s, 2H); 5.49 (s, 2H); 5.41 (s, 2H); 4.85 (broad s, 2H); 1.9–0.7 (m, 11H).
Nominal Mass Spectrum M+1: Calcd.:490. Found: 490.

EXAMPLE 9

7-Piperidinomethylene-10,
11-ethylenedioxy-20(R,S)-camptothecin (Compound 9)

The same procedure as Example 1, part (H), is used except that an equivalent amount of piperidine is used in place of dimethylamine and an equivalent amount of 7-chloromethyl-10,11-ethylenedioxy-20(R,S)-camptothecin, prepared according to Example 3, part (A), is used in place of 7-chloromethyl-10,11-methylenedioxy-20(R,S)-camptothecin.

High Resolution Mass Spectrum:
Calcd.: 504.2127. Found: 504.2129.

EXAMPLE 10

7-(4-methylpiperazinomethylene)-10,
11-ethylenedioxy-20(R,S)-camptothecin (Compound 10)

The same procedure as Example 1, part (H), is used except that an equivalent amount of 4-methylpiperazine is used in place of dimethylamine and an equivalent amount of 7-chloromethyl-10,11-ethylenedioxy-20(R,S)-camptothecin, prepared according to Example 3, part (A), is used in place of 7-chloromethyl-10,11-methylenedioxy-20(R,S)-camptothecin.

High Resolution Mass Spectrum: Calcd.: 519.2236. Found: 519.2246.

EXAMPLE 11

7-(4-methylpiperazinomethylene)-10,
11-ethylenedioxy-20(S)-camptothecin (Compound 11)

The same procedure as Example 1, part (H), is used except that an equivalent amount of 4-methylpiperazine is used in place of dimethylamine and an equivalent amount of 7-chloromethyl-10,11-ethylenedioxy-20(S)-camptothecin, prepared according to Example 4, part (A), is used in place of 7-chloromethyl-10,11-methylenedioxy-20(R,S)-camptothecin.

m.p. 261°–264° C.

Nominal Mass Spectrum M+1: Calcd.: 519. Found: 519.

EXAMPLE 12

7-Diethylaminomethylene-10,
11-methylenedioxy-20(S)-camptothecin (Compound 12)

This compound is prepared by the procedure of Example 1, part (H), except that equivalent amount of diethylamine is used in place of dimethylamine and an equivalent amount of 7-chloromethyl-10,11-methylenedioxy-20(S)-camptothecin, prepared according Example 2, part (A), is used in place of 7-chloromethyl-10,11-methylenedioxy-20(R,S)-camptothecin.

High Resolution Mass Spectrum: Calcd.: 478.1978. Found: 478.1963.

EXAMPLE 13

7-Diethylaminomethylene-10,
11-ethylenedioxy-20(R,S)-camptothecin (Compound 13)

The same procedure as Example 1, part (H), is used except that an equivalent amount of diethylamine is used in place of dimethylamine and an equivalent amount of 7-chloromethyl-10,11-ethylenedioxy-20(R,S)-camptothecin, prepared according to Example 3, part (A), is used in place of 7-chloromethyl-10,11-methylenedioxy-20(R,S)-camptothecin.

High Resolution Mass Spectrum
Calcd.: 492.2134
Found: 492.2140

EXAMPLE 14

7-Diethylaminomethylene-10,
11-ethylenedioxy-20(S)-camptothecin (Compound 14)

The same procedure as Example 1, part (H), is used except that an equivalent amount of diethylamine is used in place of dimethylamine and an equivalent amount of 7-chloromethyl-10,11-ethylenedioxy-20(S)-camptothecin, prepared according to Example 4, part (A), is used in place of 7-chloromethyl-10,11-methylenedioxy-20(R,S)-camptothecin.

High Resolution Mass Spectrum: Calcd.: 492.2134. Found: 492.2122.

EXAMPLE 15

7-N-Methylethanolaminomethylene-10,
11-methylenedioxy-20(R,S)-camptothecin (Compound 15)

The same procedure as Example 1, part (H), is used except that an equivalent amount of N-methylethanolamine is used in place of dimethylamine.

High Resolution Mass Spectrum: Calcd.: 480.1771. Found: 480.1776.

EXAMPLE 16

7-N-Methylethanolaminomethylene-10,
11-ethylenedioxy-20(R,S)-camptothecin (Compound 16)

The same procedure as Example 1, part (H), is used except that an equivalent amount of N-methylethanolamine is used in place of dimethylamine and an equivalent amount of 7-chloromethyl-10,11-ethylenedioxy-20(R,S)-camptothecin, prepared according to Example 3, part (A), is used in place of 7-chloromethyl-10,11-methylenedioxy-20(R,S)-camptothecin.

High Resolution Mass Spectrum: Calcd.: 494.1927. Found: 494.1929.

EXAMPLE 17

7-Diethanolaminomethylene-10,
11-ethylenedioxy-20(R,S)-camptothecin (Compound 17)

The same procedure as Example 1, part (H), is used except that an equivalent amount of diethanolamine is used in place of dimethylamine and an equivalent amount of 7-chloromethyl-10,11-ethylenedioxy-20(R,S)-camptothecin, prepared according to Example 3, part (A), is used in place of 7-chloromethyl-10,11-methylenedioxy-20(R,S)-camptothecin.

High Resolution Mass Spectrum: Calcd.: 524.2024. Found: 524.2026.

EXAMPLE 18

7-Diethanolaminomethylene-10,
11-ethylenedioxy-20(S)-camptothecin (Compound 19)

The same procedure as Example 1, part (H), is used except that an equivalent amount of diethanolamine is used in place of dimethylamine and an equivalent amount of 7-chloromethyl-10,11-ethylenedioxy-20(S)-camptothecin, prepared according to Example 4, part (A), is used in place of 7-chloromethyl-10,11-methylenedioxy-20(R,S)-camptothecin.

m.p. 230°-233° C.

Nominal Mass Spectrum M+1: Calcd.: 524. Found: 524.

EXAMPLE 19

7-Azetidinomethylene-10,11-methylenedioxy-20(R,S)-camptothecin (Compound 19)

The same procedure as Example 1, part (H), is used except that an equivalent amount of azetidine is used in place of dimethylamine.

m.p. >250° C.

Nominal Mass Spectrum M+1: Calcd.: 462. Found: 462.

EXAMPLE 20

7-Azetidinomethylene-10,11-methylenedioxy-20(S)-camptothecin (Compound 20)

This compound is prepared by the procedure of Example 1 except in parts (G) an equivalent amount of tricyclic ketone (S) is used in place of tricyclic ketone (R,S), and in part (H) and equivalent amount of azetidine is used in place of dimethylamine.

High Resolution Mass Spectrum: Calcd.: 462.1665. Found: 462.1667.

EXAMPLE 21

7-Thiomorpholinomethylene-10,11-ethylenedioxy-20(S)-camptothecin (Compound 21)

The same procedure as Example 1, part (H), is used except that an equivalent amount of thiomorpholine is used in place of dimethylamine and an equivalent amount of 7-chloromethyl-10,11-ethylenedioxy-20(S)-camptothecin, prepared according to Example 4, part (A), is used in place of 7-chloromethyl-10,11-methylenedioxy-20(R,S)-camptothecin.

m.p. 249°-252° C.

Nominal Mass Spectrum M+1: Calcd.: 522. Found: 522.

EXAMPLE 22

7-Azetidinomethylene-10,11-ethylenedioxy-20(S)-camptothecin (Compound 22)

The same procedure as Example 1, part (H), is used except that an equivalent amount of azetidine is used in place of dimethylamine and an equivalent amount of 7-chloromethyl-10,11-ethylenedioxy-20(S)-camptothecin, prepared according to Example 4, part (A), is used in place of 7-chloromethyl-10,11-methylenedioxy-20(R,S)-camptothecin.

m.p. 208–210 (decomp.)

Low Resolution Mass Spectrum: 476.2 (ES).

EXAMPLE 23

7-(4-Methylpiperazinomethylene)-10,11-methylenedioxy-20(S)-camptothecin (Compound 23)

This compound is prepared by the procedure of Example 1 except in parts (G) an equivalent amount of tricyclic ketone (S) is used in place of tricyclic ketone (R,S), and in part (H) and equivalent amount of 4-methylpiperazine is used in place of dimethylamine.

High Resolution Mass Spectrum: Calcd.: 505.2083. Found: 505.2087.

EXAMPLE 24

7-Trifluoroacetamidomethylene-10,11-ethylenedioxy-20(S)-camptothecin (Compound 24)

(A)

2'-Amino-4',5'-methylenedioxy-2-trifluoroacetamidoacetophenone

Trifluoroacetamine (227 mg, 2 mmole) is added to a solution of cesium carbonate (1.63 g, 5 mmole) in anhydrous acetonitrile (15 ml) at room temperature under nitrogen. 2'-Amino-4',5'-methylenedioxy-2-chloroacetophenone is then added and the mixture is placed in a preheated oil bath set at 90° C. for 30 minutes. The reaction is cooled to room temperature and poured directly onto a silica plug (15 g) in a scintered glass funnel. The silica is washed two times with EtOAc and the volatiles from the combined washes are removed in vacuo. Diethyl either is used to triturate the residue to afford a light orange solid which is collected by filtration and dried under vacuum. (498 mg, 86%). Mp=219°-220° C. $^1$H NMR (300 MHz, DMSO-$^6$): δ 4.44 (d, 2H); 5.96 (s, 2H); 5.96 (s, 2H); 6.35 (s, 1H); 7.21 (s, 1H); 7.40 (bs, 2H); 9.59 (t, 1H). Nominal mass expected: MH+ =291 m/z. found MH+ =291 m/z.

(B)

2'-Amino-4',5,-ethylenedioxy-2-trifluoroacetamidoacetophenone

This compound is prepared as in the method above except an equivalent amount of 2'-amino-4',5'-ethylenedioxy-2-chloroacetophenone is used in place of 2'-amino-4',5'-methylenedioxy-2-chloroacetophenone. A green solid is isolated in 74% yield. Mp=154°-155° C. $^1$H NMR (300 MHz, CDCl$_3$): δ 4.08 (m, 2H); 4.13 (m, 2H); 4.60 (d, 2H); 6.0 (bs, 2H); 6.08 (s, 1H); 7.04 (s, 1H); 7.60 (t, 1H). Nominal mass expected: MH+ =305 m/z. Found: MH+ =305 m/z.

(C)

10,11-Ethylenedioxy-7-trifluoroacetamidomethylene-20(S)-camptothecin

2'-Amino-4',5'-ethylenedioxy-2-trifluoroacetamidoacetophenone (71 mg, 0.234 mmole), tricyclic ketone (S) (61 mg, 0.234 mmole), and anhydrous toluene (2.0 ml) are combined at 60° C. under nitrogen. A catlytic amount of both glacial acetic acid and p-toluenesulfonic acid monohydrate are added before increasing the reaction temperature to reflux. The reaction refluxes for 16 hrs and is then cooled to ambient temperature. A green-yellow solid is collected by filtration, washed with ethanol and diethyl ether, and dried in vacuo. (101 mg, 84%) Mp=249° C. $^1$H NMR (300 MHz, DMSO-d6): δ 0.91 (t, 3H); 1.91 (m, 2H); 4.40 (s, 4H); 4.83 (d, 2H); 5.39 (s, 2H); 5.41 (s, 2H); 6.48 (s, 1H); 7.22 (s, 1H); 7.58 (s, 1H); 7.77 (s, 1H); 10.20 (t, 1H). Nominal mass expected: MH+ =532 m/z. Found: MH+ =532 m/z.

EXAMPLE 25

7-Trifluoroacetamidomethylene-10,11-methylenedioxy-20(S)-camptothecin (Compound 25)

This compound is prepared by the method of Example 24 above except an equivalent amount of 2'-amino-4',5'-methylenedioxy-2-trifluoroacetamidoacetophenone is used in place of 2'-amino-4',5'-ethylenedioxy-2-trifluoroacetamidoacetophenone. A green-yellow solid is isolated in 15% yield mp=238° C. (d). $^1$H-300 NMR (DMSO-d6): δ 0.91 (t, 3H); 1.95 (m, 2H); 4.92 (s, 2H); 5.38 (s, 2H); 5.40 (s, 2H); 6.28 (S, 2H); 6.49 (s, 1H); 7.13 (s, 1H); 7.58 (s, 1H); 7.78 (s, 1H); 10.21 (t, 1H). Nominal mass expected: MH+=518 m/z. Found MH+=518 m/z.

EXAMPLE 26

7-Aminomethylene-10,11-ethylenedioxy-20(S)-camptothecin dihydrochloride (Compound 26)

7-trifluoroacetamidomethylene-10,11-ethylenedioxy-20(S)-camptothecin (65 mg, 0.12 mmole) is heated to 105° C. in aqueous 2N hydrochloric acid (1.2 ml) for 20 minutes in an open flask. the volatiles are removed in vacuo and the residue is triturated with ethyl acetate and collected by filtration. The bright yellow solid is washed with ethyl acetate (3 ml), ethanol (2 ml) and diethyl ether (2 ml) and dried in vacuo to afford 62 mg (100%). mp>300° C. $^1$H NMR (300 MHz, DMSO-d6): δ 0.90 (t, 3H); 1.95 (m, 2H); 4.41 (s, 4H); 4.61 (d, 2H); 5.40 (s, 2H); 5.45 (s, 2H); 7.24 (s, 1H); 7.60 (s, 1H); 7.81 (s, 1H); 8.40 (bs, 2H). Nominal mass expected: MH+=436 m/z. Found MH+=436 m/z.

EXAMPLE 27

7-Aminomethylene-10,11-methylenedioxy-20(S)-camptothecin dihydrochloride (Compound 27)

This compound is prepared by the method of Example 26 above except an equivalent amount of 7-trifluoroacetamidomethylene-10,11-methylenedioxy-20(S)-camptothecin is used in place of 7-trifluoroacetamidomethylene-10,11-ethylenedioxy-20(S)-camptothecin. A golden yellow solid is isolated in quantitative yield. Mp=270° C. (d). $^1$H NMR (300 MHz, DMSO-d6): δ 0.90. (t, 3H); 1.9 (m, 2H); 4.6 (m, 2H); 5.4 (s, 2H); 5.5 (s, 2H); 6.3 (s, 2H); 7.2 (s, 1H); 7.6 (s, 1H); 7.9 (s, 1H); 8.4 (bs, 2H). Nominal mass expected: MH+=422 m/z. Found: MH+=422 m/z.

EXAMPLE 28

7-tert-Butyloxycarbonyl-piperazinomethylene-10,11-ethylenedioxy-20(S)-camptothecin (Compound 28)

To a −50° C. solution of (S)-(−) -10, 11-ethylenedioxy-7-chloromethylcamptothecin (35.8 mg, 78.7×10$^{-3}$ mmol) was added dropwise tert-butyl-l-piperazinecarboxylate (34.6 mg, 186×10$^{-3}$ mmol) in N,N-dimethylformamide (DMF) (0.45 mL). The dark brown reaction mixture was stirred at −50° C. for 10 min, and allowed to warm to 0° C. Additional tert-butyl-l-piperazinecarboxylate (8 mg, 43×10$^{-3}$ mmol) in DMF (0.2 mL) was added, and the mixture was allowed to warm to ambient temperature. The mixture was stirred for an additional 90 min, and the solvent was removed with a rotary evaporator to afford the crude product as a brown residue. Purification by silica gel chromatography (eluting with 100% ethyl acetate) afforded 20.7 mg (58% yield) of the product as a pale yellow solid. $^1$H NMR (300 MHz, CDCl$_3$): δ 1.04 (t, 3H, J=7); 1.45 (s, 9H); 1.87 (m, 2H); 2,46 (s, 4H); 3.41 (s, 4H); 3.94 (s, 2H); 4.43 (s, 4H); 5.29 (s, 2H); 5.30 (d, 1H, J=16); 5.75 (d, 1H, J=16); 7.59 (s, 1H); 7.65 (s, 1H); 7.73 (s, 1H). Nominal mass spectrum (M+1): 605.

EXAMPLE 29

7-Piperazinomethylene-10, 11-ethylenedioxy-20(S)-camptothecin trifluoroacetic acid salt (Compound 29)

To a 0° C. solution of 7-tert-butyloxycarbonyl-piperazinomethyl-10, 11-ethylenedioxy-20(S)-camptothecin (16.7 mg, 27.6×10$^{-3}$ mmol) in dry CH$_2$Cl$_2$ (5.0 mL) was added trifluoroacetic acid (0.5 mL). The deep yellow solution was allowed to warm to ambient temperature and stirred for 14 h. The mixture was concentrated with a rotary evaporator, and the residue was purified by reverse phase HPLC (Rainin Dynamax 60A column, eluting with 49:10:2.5:1 water/acetonitrile/THF/trifluoroacetic acid) to afford, after concentration and lyophylization of the major UV active peak (monitoring at 254 nm), 21.7 mg of the product as a yellow fluffy powder. $^1$H NMR (300 MHz, DMSO-d$_6$): δ 0.88 (t, 3H, J=7); 1.87 (m, 2H); 2.60–2.80 (m, 4H); 3.00–3.20 (bs, 4H); 5.29 (s, 2H); 5.41 (s, 2H); 6.5 (bs, 1H); 7.25 (s, 1H); 7.56 (s, 1H); 7.80 (s, 1H); 8.50 (bs, 2H).
Nominal mass spectrum (M+1): 505.
mp: 315° C.(d)

EXAMPLE 30

7-(α, α, α-Trifluoro-m-tolyl)-piperazinomethylene-10, 11-ethylenedioxy-20(S)-camptothecin (Compound 30)

A solution of 7-chloromethyl-10,11-ethylenedioxy-20(S)-camptothecin (5.2 mg, 11.4×10$^{-3}$ mmol) in anhydrous DMSO (200 uL) was added dropwise to a 0° C. solution of 1-(α,α,α-trifluoro-m-tolyl)-piperazine (10 uL, 53×10$^{-3}$ mmol) in anhydrous toluene (500 uL). The dark brown mixture was stirred at 0° C. for 90 min, and allowed to warm to ambient temperature. The solvent was removed with a rotary evaporator and further pumping under high vacuum to leave the crude product, which was purified by silica gel chromatography (eluting with 100% ethyl acetate followed by 6:5:1 ethyl acetate/chloroform/methanol) to afford 3.7 mg (50% yield) of the product as a pale yellow solid residue. $^1$H NMR (200 MHz, DMSO-d$_6$); δ 0.90 (t, 3H, J=7); 1.95 (q, 2H, J=7); 2.60–2.70 (m, 4H); 3.20–3.30 (m, 4H); 4.10 (s, 2H); 4.50 (s, 4H); 5.30; (s, 2H); 5.45 (s, 2H); 6.55 (s, 1H); 7.40 (t, 1H, J=7); 7.60 (s, 1H); 7.85 (s, 1H).
Nominal mass spectrum (M+1): 649.

EXAMPLE 31

7-(2-Methoxyphenyl-piperazino)methylene-10, 11-ethylenedioxy-20(S)-camptothecin (Compound 31)

To a 0° C. solution of 2-methoxyphenylpiperazine (17.9 uL, 102×10$^{-3}$ mmol) in anhydrous toluene (1 mL) at 0° C. was added a solution of 7-chloromethyl-10, 11-ethylenedioxy-20(S)-camptothecin (10 mg, 22×10$^{-3}$ mmol) in DMSO (200 uL). The dark mixture was stirred at 0° C. for 10 min, and allowed to warm to ambient temperature and stirred for 3 h. The reaction mixture was concentrated with a rotary evaporator and the residual solvent was removed by pumping under high vacuum to afford the crude product. Purification by silica gel chromatography (eluting with 1:1 hexane/ethylacetate followed by 6:5:1 ethylacetate/chloroform/methanol) afforded 3.4 mg (25% yield) of the product as a yellow solid. $^1$H NMR (200 MHz, CDCl$_3$): δ 1.05 (t, 3H, J=7); 1.90 (m, 2H); 2.75 (bs, 4H), 3.10 (bs, 4H), 3.75 (s, 3H); 3.85 (s, 3H); 4.01 (bs, 2H); 5.35 (s, 1H); 5.30 (d, 1H, J=18); 5.35 (s, 1H); 5.75 (d, 1H, J=18); 6.80–7.00 (m, 4H); 7.60 (s, 1H); 7.65 (s, 1H); 7.75 (s, 1H).

Nominal mass spectrum (M+1): Calcd.: 611. Found: 611

EXAMPLE 32

7-Phenylpiperazinomethylene-10,11-ethylenedioxy-20(S)-camptothecin (Compound 32)

To a 0° C. solution of phenylpiperazine (15.6 uL, $102 \times 10^{-3}$ mmol) in anhydrous toluene (1 mL) was added a solution of 7-chloromethyl-10,11-ethylenedioxy-20(S)-camptothecin (10.6 mg, $22 \times 10^{-3}$ mmol) in DMSO (300 uL). The dark mixture was stirred at 0° C. for 10 min, and allowed to warm to ambient temperature and stirred for 3 h. The mixture was concentrated with a rotary evaporator, and the residual solvent was further removed by pumping under high vacuum to afford the crude product as a dark residue. Purification by silica gel chromatography (eluting with 1:1 hexane/ethyl acetate followed by 6:5:1 ethyl acetate/chloroform/methanol) afforded 3.6 mg (30% yield) of the product as a yellow solid residue. $^1$H NMR (200 MHz, CDCl$_3$): δ 1.00 (t, 3H, J=7); 1.90 (m, 2H); 2.75 (bs, 4H); 3.20 (bs, 4H); 3.75 (s, 1H); 4.05 (s, 2H); 4.45 (bs, 4H); 5.35 (s, 2H); 5.30 (d, 1H, J=18); 5.35 (s, 2H); 5.75 (d, 1H); 6.80–7.00 (m, 3H); 7.20–7.35 (m, 2H); 7.60 (s, 1H); 7.65 (s, 1H); 7.80 (s, 1H). Nominal mass spectrum (M+1): 581.

EXAMPLE 33

2'-Amino-4',5'-methylenedioxy-2-dimethylaminoacetophenone

2'-Acetylamino-4',5'-methylenedioxy-2-chloroacetophenone, prepared in Example 1, part (B), is reacted with an excess of dimethylamine under similar conditions as taught in Example 1, part (H), to yield 2'-acetylamino-4',5'-methylenedioxy-2-dimethylaminoacetophenone which is turn is deprotected by the procedure of Example 1, part (E), to yield 2'-amino-4',5'-methylenedioxy-2-dimethylaminoacetophenone.

Nominal Mass Spectrum M+1: Calcd.: 223. Found: 223.

EXAMPLES 34–38

The following compounds of formula (I) are prepared by the procedure taught in Scheme I or Scheme IA, in an analogous manner to Examples 1–22, using the appropriate intermediate compounds of formulas (II), (III), (IV) and (V).

34: 7-(Methyl-2-methoxyethylaminomethylene)-10, 11-methylenedioxy-20(R,S)-camptothecin, 35: 7-Cyclohexylaminomethylene-10, 11-methylenedioxy-20(R)-camptothecin, 36: 7-(2-Butenyl)aminomethylene-10, 11-methylenedioxy-20(R,S)-camptothecin, 37: 7-Cyclohexylmethylaminomethylene-10, 11-ethylenedioxy-20(R)-camptothecin and 38: 7-Thiazolidinomethylene-10, 11-methylenedioxy-20(R,S)-camptothecin.

EXAMPLE 39

Pharmaceutical Formulations

| (A) Transdermal System | |
|---|---|
| Ingredients | Amount |
| Active compound | 600.0 mg |

| (A) Transdermal System -continued | |
|---|---|
| Ingredients | Amount |
| Silicone fluid | 450.0 mg |
| Colloidal silicone dioxide | 25.0 mg |

The silicone fluid and active compound are mixed together and the colloidal silicone dioxide is reacted with to increase viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene), polyvinyl acetate or polyurethane, and an impermeable backing membrane made of a polyester multilaminate. The system described is a 10 sq. cm patch.

| (B) Oral Tablet | |
|---|---|
| Ingredients | Amount |
| Active compound | 200.0 mg |
| Starch | 20.0 mg |
| Magnesium Stearate | 1.0 mg |

The active compound and the starch are granulated with water and dried. Magnesium stearate is added to the dried granules and the mixture is thoroughly blended. The blended mixture is compressed into a tablet.

| (C) Suppository | |
|---|---|
| Ingredients | Amount |
| Active compound | 150.0 mg |
| Theobromine sodium salicylate | 250.0 mg |
| Witepsol S55 | 1725.0 mg |

The inactive ingredients are mixed and melted. The active compound is then distributed in the molten mixture, poured into molds and allowed to cool.

| (D) Injection | |
|---|---|
| Ingredients | Amount |
| Active Compound | 20.0 mg |
| Buffering Agents | q.s. |
| Propylene glycol | 0.4 |
| Water for injection | 0.6 mL |

The active compound and buffering agents are dissolved in the propylene glycol at about 50° C. The water for injection is then added with stirring and the resulting solution is filtered, filled into an ampule, sealed and sterilized by autoclaving.

| (E) Capsule | |
|---|---|
| Ingredients | Amount |
| Active Compound | 200.0 mg |
| Lactose | 450.0 mg |
| Magnesium stearate | 5.0 mg |

The finely ground active compound is mixed with the lactose and stearate and packed into a gelatin capsule.

We claim:

1. A method of preparing a compound of formula (I),

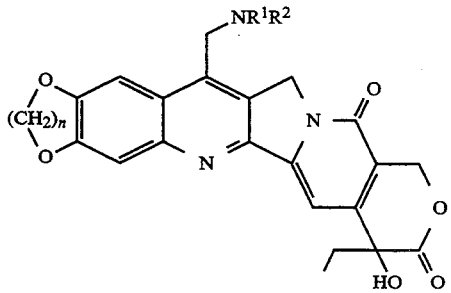

(I)

wherein:

n represents the integer 1 or 2;

$R^1$ represents independently, hydrogen, lower alkyl, ($C_{3-7}$)cycloalkyl, ($C_{3-7}$)cycloalkyl lower alkyl, lower alkenyl, hydroxy lower alkyl or lower alkoxy lower alkyl; and $R^2$ represents hydrogen, comprising:

a) treating a compound of formula (IVb),

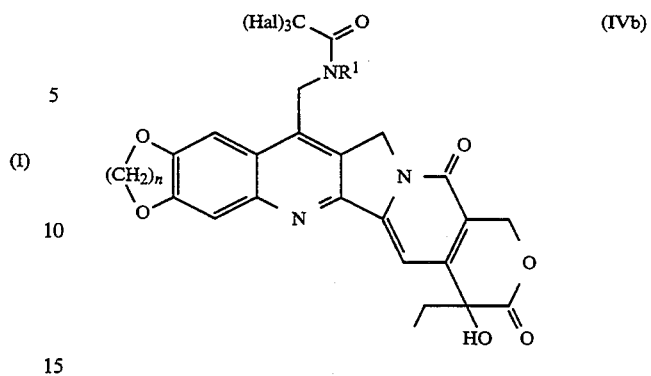

(IVb)

wherein Hal represents fluoro, chloro, bromo or iodo, with hydrochloric or sulfuric acid to yield a compound of formula (1b);

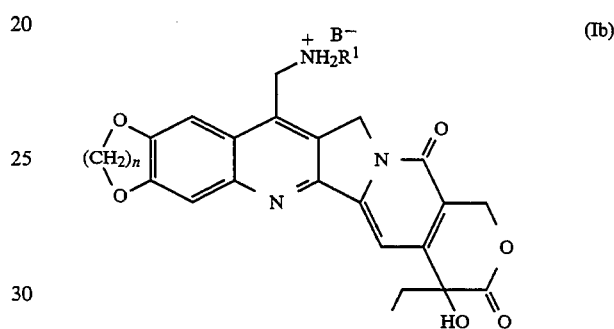

(Ib)

wherein B- is a hydrochloride or sulfuric acid anion;

b) treatment of a compound formula (1b), with or without isolation, with about one equivalent of an alkali metal hydroxide or alkali metal carbonate.

2. The method of claim 1 wherein n is 1 and $R^1$ is hydrogen.

3. The method of claim 1 wherein n is 2 and $R^1$ is hydrogen.

4. The method of claim 1 wherein said alkali metal hydroxide is sodium hydroxide.

5. The method of claim 1 wherein said alkali metal carbonate is potassium carbonate.

* * * * *

UNITED STATES PATENT AND TRADEMARK OFFICE
CERTIFICATE OF CORRECTION

PATENT NO. : 5,342,947
DATED : August 30, 1994
INVENTOR(S) : Lackey et al.

It is certified that error appears in the above-identified patent and that said Letters Patent is hereby corrected as shown below:

Column 11, line 43, change "Theodore w. Greene" to --Theodore W. Greene--.

Column 11, lines 58-59, change "an aralkyl groups" to --an aralkyl group--.

Column 12, line 10, change "by carried out" to --be carried out".

Column 12, line 25, change "may also be used of the introduction" to --may also be used for the introduction--.

Column 12, line 43, change "Scheme I or Scheme I, be purified" to -Scheme I or Scheme IA may be purified--.

Column 14, line 55, change "other endocrine gland" to --other endocrine glands--.

Column 18, line 3, change "5'(R,S)-1,5-Dioxo-(5'-ethyl-5'hydroxy-2'H, 5'H,6'H,6-oxopyrano" to --5'(R,S)-1,5-Dioxo-(5'-ethyl-5'hydroxy-2'H, 5'H,6'H-6-oxopyrano--.

Column 19, line 56, change "Found 464,1833" to --Found 464.1833--.

Column 20, line 12, change "in place of" to --is used in place of--,

Column 21, line 54, change "prepared according Exam-" to --prepared according to Exam---.

Column 24, line 21, change "Diethyl either" to --Diethyl ether--.

Column 24, line 24, change "(300 MHz, DMSO-6)" --(300 MHz, DMSO-d6)--.

Column 24, line 27, change "found MH+=291 m/z" to --Found MH+=291 m/z--.

UNITED STATES PATENT AND TRADEMARK OFFICE
CERTIFICATE OF CORRECTION

PATENT NO. : 5,342,947
DATED : August 30, 1994
INVENTOR(S) : Lackey et al.

It is certified that error appears in the above-identified patent and that said Letters Patent is hereby corrected as shown below:

Column 25, line 16, change "the volatiles are removed" to --The volatiles are removed--.

Column 25, line 22, change "mp>300°C" to --Mp>300°C--,

Column 25, lines 39, change "§0.90. (t,3H)" to --§0.90 (t,3H)--.

Column 26, line 42, change "NMR(200MHz, DMSO-$d_6$); §0.90" to --NMR(200MHz, DMSO-$d_6$): §0.90--.

Column 27, line 39, change "which is turn is deprotected by" to --which in turn is deprotected by--.

Signed and Sealed this

Sixteenth Day of May, 1995

BRUCE LEHMAN

*Attest:*

*Attesting Officer*  *Commissioner of Patents and Trademarks*